United States Patent [19]

Gall et al.

[11] Patent Number: 4,908,843
[45] Date of Patent: Mar. 13, 1990

[54] LIGHT DISTRIBUTOR FOR AN X-RAY DIAGNOSTICS INSTALLATION

[75] Inventors: Arthur Gall, Langensendelbach; Gerhard Kuetterer, Erlangen; Helmut Richter, Baiersdorf, all of Fed. Rep. of Germany

[73] Assignee: Siemens Aktiengesellschaft, Berlin and Munich, Fed. Rep. of Germany

[21] Appl. No.: 335,561

[22] Filed: Apr. 10, 1989

[30] Foreign Application Priority Data

May 25, 1988 [DE] Fed. Rep. of Germany ....... 8806828

[51] Int. Cl.⁴ .............................................. H05G 1/64
[52] U.S. Cl. ........................................ 378/99; 378/62; 350/171; 350/623; 350/626
[58] Field of Search .............. 378/42, 62, 99; 358/111; 350/169-174, 422, 623-626

[56] References Cited

U.S. PATENT DOCUMENTS

| | | | |
|---|---|---|---|
| 2,285,515 | 6/1942 | Hurley | 350/171 |
| 3,622,786 | 11/1969 | Walker et al. | 378/99 |
| 3,684,354 | 8/1972 | Koch | 350/289 |
| 4,237,492 | 12/1980 | Roth et al. | 358/108 |
| 4,383,328 | 5/1983 | Kurihara et al. | 378/42 |
| 4,413,352 | 11/1983 | Nishio | 378/42 |
| 4,544,949 | 10/1985 | Kurihara | 378/42 |
| 4,588,254 | 5/1986 | Menke et al. | 350/172 |

FOREIGN PATENT DOCUMENTS 0051430 5/1982 European Pat. Off.
0175663 3/1986 European Pat. Off.

*Primary Examiner*—Janice A. Howell
*Assistant Examiner*—John C. Freeman
*Attorney, Agent, or Firm*—Hill, Van Santen, Steadman & Simpson

[57] ABSTRACT

A light distributor for use in an X-ray diagnostics installation wherein a light image corresponding to an X-ray image is generated by an X-ray image intensifier, and the light image is to be recorded using a number of different image recorders as a housing with input optics facing toward the X-ray image intensifier for generating a parallel light beam path, and has at least two movable mirror surfaces secured flat on a carriage. The carriage and mirror surfaces are arangement obliquely in a plane which is parallel to the beam path, and the carriage is displaceable along guides within this plane so that one of the mirror surfaces can be laterally moved into the beam path to deflect the light from the image intensifier onto a desired image recorder. At least one of the mirror surfaces is partially reflecting.

13 Claims, 3 Drawing Sheets

LIGHT DISTRIBUTOR FOR AN X-RAY DIAGNOSTICS INSTALLATION

BACKGROUND OF THE INVENTION

1. Field of the Invention

The present invention is directed to a light distributor for an x-ray diagnostics installation for directing light from the output screen of an x-ray image intensifier onto a plurality of pick-up components, such as cameras attached to the housing of the light distributor.

2. Related Application

The subject matter of the present application is related to the subject matter of co-pending U.S. application Ser. No. 216,201, filed July 7, 1988 (Arthur Gall and Karl Weiss) entitled "Light Distributor For An X-Ray Diagnostics Installation."

3. Description of the Prior Art

For displaying and/or permanently recording x-ray images in an x-ray diagnostics installation, various different types of pick-up components, such as cameras, are arranged to receive the light, corresponding to an x-ray image, from the output screen of an x-ray image intensifier. Frequently more than one type of display and/or recording is desired, such as, for example, a video display, a moving picture (strip film) or a photographic picture (sheet film). Thus as many as three cameras, namely a video camera, a motion picture camera and a photographic camera, may be necessary to couple to the x-ray image intensifier to obtain all of the desired formats. Image recording via these pick-up components may be undertaken simultaneously or in sequence. This requires that the light from the output screen of the x-ray image intensifier be divided or distributed so as to reach each of the pick-up components.

A light distributor is disclosed in U.S. Pat. No. 4,383,328 which distributes the light from the output image of an x-ray image intensifier onto two motion pictures cameras and onto one video camera. A pivotable, semi-reflective mirror splits the light from the output screen of the image intensifier onto the two motion picture cameras. The pivotable mirror, however, remains within the beam path of one of the motion picture cameras in its standby position. A 100% reflecting mirror can be disposed in front of the pivotable mirror in its standby position, the reflecting mirror being disposed perpendicularly relative to the beam path of x-ray image intensifier. A mirror arrangement having a rotatable mirror tilted at a angle of 45% and having a reflection of 90% can be introduced into the beam path in front of the 100% reflecting mirror, the rotatable mirror permitting selecting deflection of the beam path onto one of the motion picture cameras or onto the video camera.

One purpose of the light distributor disclosed in U.S. Pat. No. 4,383,328 is to provide a more compact structure in comparison to previously known light distributors, so that the vertex distances of the lenses of the motion picture cameras relative to the input optics which receives the light from the x-ray image intensifier can be maintained small in order to achieve a good image quality. This is important because light losses increase with an increase in the vertex distance of the lens. In the structure of U.S. Pat. No. 4,383,328, however, the introduction of mirrors following each other in different planes in the beam path still undesirably increases the vertex distance. Moreover, it is difficult to maintain pivotable mirrors as used in the structure of U.S. Pat. No. 4,383,238 stable against jolts during operation. Additionally, this known light distributor must include a plurality of motors for actuating the mirrors, giving the light distributor a relatively complicated structure and a relatively high weight. Moreover, the structural length of the combination consisting of the x-ray image intensifier and the pick-up components is increased, since one of the pick-up components, for example the first motion picture camera, is situated in the direct beam path of the x-ray image intensifier. In some instances, the height of the examination room in which the installation is contained will not be sufficient, given the use of devices disposed beneath the patient support table, and the presence of an additionally ceiling support, which further add to the overall height of the combination.

SUMMARY OF THE INVENTION

It is an object of the present invention to provide a light distributor for distributing light from the output screen of an x-ray image intensifier in an x-ray diagnostics installation to one or more image recording devices, wherein the respective vertex distances of the lenses of each image recording device can be maintained small, and wherein the overall light distributor unit has a low weight.

These and other objects are achieved in accordance with principles of the present invention in a light distributor having a displaceable carriage on which two mirror surfaces are secured flat, with the carriage and mirror surfaces being arranged obliquely in a plane which is parallel to the beam path from the x-ray image intensifier. One of the mirror surfaces can be laterally moved into the beam path by a drive system operating on the carriage, and at least one of the mirror surfaces is partially reflecting. As a result of the oblique arrangement one plane, the mirror surfaces and the mounting structure contribute little to the length of the vertex distance, so that a highly compact and lightweight structure is obtained.

An even more compact structure is obtained in an embodiment wherein the mirror surfaces are displaceable in the plane of the beam path of the input optics and in the plane of the beam path which is deflected by the particular mirror surface. As a result, even though the two mirror surfaces may be placed side-by-side, or behind one another, this contributes little to increasing the structure size, because the mirror surfaces are essentially guided between the components coupled to the light distributor.

A multi-channel light distributor is obtained in a further embodiment wherein an additional, moveable mirror surface is arranged in the beam path, which is connected to the housing in a rotatable or pivotable fashion. The further movable mirror surface is arranged in the beam path following the previously described two mirror surfaces which are displaceable in a plane. A stable arrangement of the moveable mirror surfaces which is easy to adjust is obtained in an embodiment wherein two guide rods are provided disposed oblique relative to the parallel beam path between the input optics and one pick-up component, with the guide rods surrounding the pick-up component. The carriage has a channeled which rides on and surrounding one of the guide rods, and has opposed rollers disposed on opposite sides of the other guide rod.

A drive system for displacing the carriage for the moveable mirror surfaces may include a crank drive or crank linkage, having one side secured to the housing, and operated by a rotary drive.

An even more space-saving embodiment of the light distributor is achieved wherein one of the optical systems is an angular optics system, which effects a lateral deflection of the beam path by an angle.

A more economic embodiment which achieves the same result includes input optics which is a "straight line" optics system, with a fixed mirror secured in the housing of the light distributor which laterally deflects the beam path by an angle. Further structural height can be eliminated when this angle is approximately 80°. The video camera may preferably be coupled by the displaceable mirrors in an embodiment wherein the partially reflecting mirror exhibits a reflection of approximately 20%.

A four-channel light distributor having a short vertex distance for a coupled video camera, and having three camera channels, each camera channel having an associated pick-up component (image recording component) attached to the light distributor at respectively different locations, in an embodiment wherein the two mirror surfaces attached to the carriage are disposed in the beam path from the image intensifier, the surfaces deflecting at least a portion of the light incident from the input optics onto a video camera coupled to the light distributor, and a further rotatable mirror surface following the two mirror surfaces, which can be held in three positions. The beam path from the output image of the x-ray image intensifier can be alternatively directed onto three additional pick-up components attached to the housing of the light distributor by the rotatable mirror surface. An optimum video mode with optional observation is obtained when one of the mirror surfaces has a reflection of 100%, and the other is a partially reflecting mirror surface with a reflection of 20%.

DESCRIPTION OF THE PREFERRED EMBODIMENTS

Figure 1:
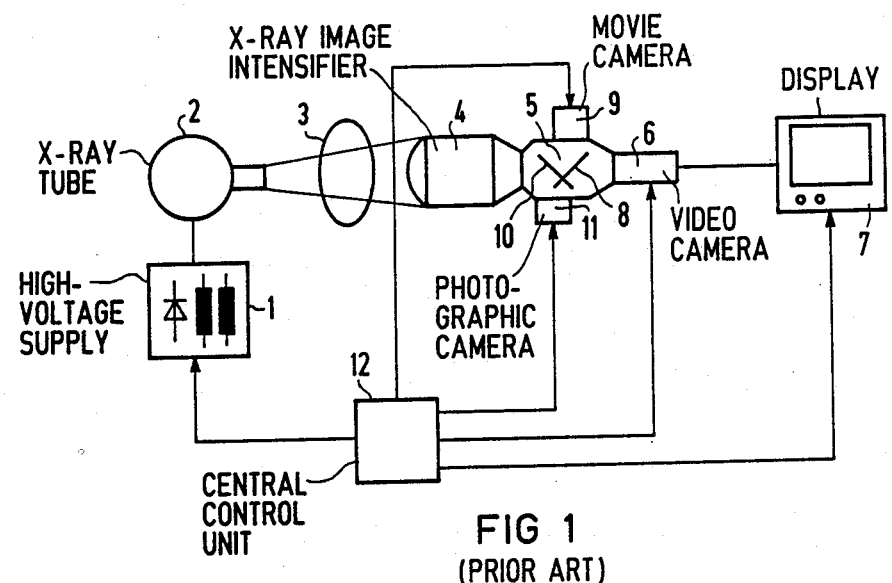
FIG. 1 is a block diagram of a conventional x-ray diagnostics installation including a conventional light distributor.

The relevant components of a conventional x-ray diagnostics installation are schematically shown in FIG. 1. The installation includes a high voltage supply 1 which drives an x-ray tube 2. The x-ray tube 2 generates an x-ray beam in which an examination subject 3 is disposed. Radiation attenuated by the examination subject 3 is incident on the input luminescent screen of an x-ray image intensifier 4. The output screen of the x-ray image intensifier 4 generates a light image corresponding to the x-ray image. A light distributor 5 is connected to the output screen of the x-ray image intensifier 4. A video camera 6 is connected to one optical output port of the light distributor 5 as a first image recording component, and generates a video signal so that the output image from the x-ray image intensifier 4 can be displaced on a television monitor 7. A first, moveable mirror 8 can be introduced into the beam path from the output screen of the x-ray image intensifier 4 so that the output image of the x-ray image intensifier 4 can, for example, be deflected onto a motion picture camera 9 as a second image recorder. A second, movable mirror 10, which can also be introduced into the beam path, deflects the light in a different direction, so that the output image of the x-ray image intensifier 4 can, for example, be directed to a photographic camera 11 as a third image recorder. A central control unit 12 controls and synchronizes the operation of the high voltage supply 1, the video chain consisting of the camera 6 and the display 7, the mirrors 8 and 10, and the cameras and 9 and 11.

If such an x-ray diagnostics installation is arranged as an under-the-table apparatus, i.e., the x-ray tube 2 is disposed beneath a patient support table and the image intensifier/image recorder unit is disposed above the patient support table, a maximum room height which is required is determined by the height of the fully raised x-ray image intensifier/image recorder unit. The video camera 6, which is directed away from the x-ray image intensifier 4 along a straight line, increases the maximum space requirement to an undesirable extent.

A light distributor 5 constructed in accordance with the principles of the present invention is shown in the remaining figures which is intended to replace the light distributor 5 in the known installation shown in FIG. 1.

Figure 2:
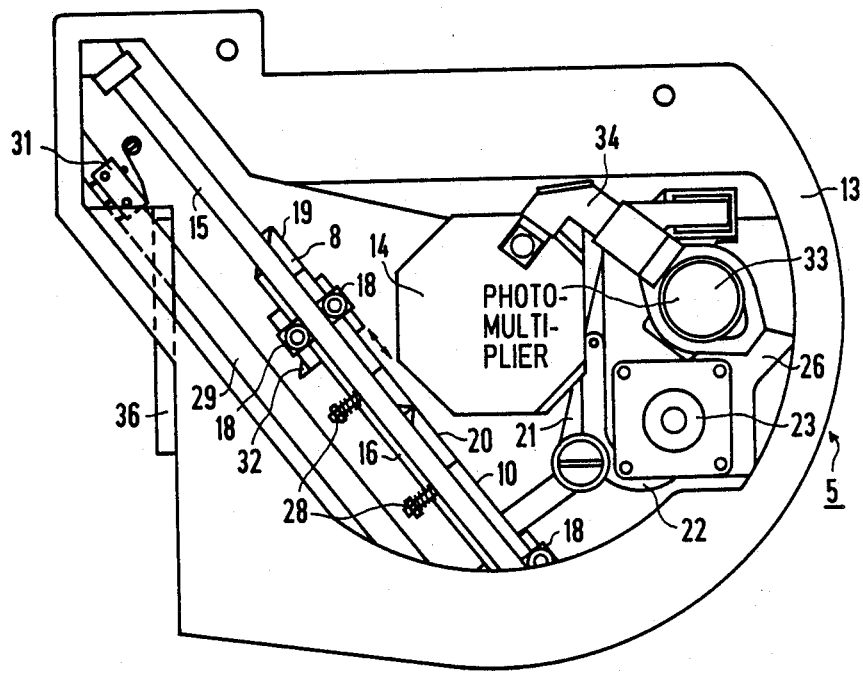
FIG. 2 is a view of a two-channel light distributor constructed in accordance with the principles of the present invention as seen from the x-ray image intensifier.

In the embodiment of FIG. 2, a housing 13 of the light distributor 5 is shown as seen from the x-ray image intensifier 4. A first mirror 14 is disposed inside the housing in the beam path from the x-ray image intensifier. As is known, input optics will be provided in the beam path between the output screen of the x-ray image intensifier 4 and the mirror 14, so that a parallel beam path is generated which is incident on the mirror 14. The mirror 14 deflects the light incident thereon at substantially a right angle onto an image recorder (not shown) which can be coupled to the housing 13 at a mount 36. The first mirror 14 can be rigidly connected to the housing 13. The beam path between the first mirror 14 and the coupled image recorder is surrounded by two guide rods 15, on which a carriage 16 is displaceable mounted. As can best be seen in FIG. 3, which shows a plan view of the light distributor 5 the carriage 16 has a channeled slide 17 which surrounds, or partially surrounds, one of the guide rods 15, and has rollers 18 at an opposite side which surround the second guide rod 15 on both sides, functioning as bearings. The carriage 16 is thus displaceable along the guide rods 15. Two mirrors 8 and 10 are secured flat on the carriage 16, and function as moveable mirror surfaces 19 and 20. The two moveable mirror surfaces 19 and 20 can be individually displaced into the beam path between the first mirror 14 and the coupled image recorder by a crank drive, so that the mirror surfaces 19 and 20 deflect the light onto another image recorder coupled to the housing 13 at a further mount 35.

The first mirror surface 19 may be 100% reflective so that, in the position shown in FIG. 2, the first mirror surface 19 conducts all of the light in the parallel beam path from the image intensifier to the optics of the image recorder coupled at the mount 35. Thus all of the light from the output luminescent screen of the x-ray image intensifier 4, with the exception of slight losses, is conducted to the target of the image recorder coupled to the housing at the mount 35.

The second movable mirror surface 20 may be approximately 20% reflective, so that a substantial portion of the light incident thereon is transmitted therethrough, whereas only a small portion is reflected. As described below, the carriage 16 is displaced along the guide rods 15 so that the mirror surface 20 of the second moveable mirror 10 is situated in the parallel beam path from the mirror 14, the second mirror surface 20 permitting 80% of the light from the output screen of the x-ray image intensifier 4 to pass therethrough to the image recorder coupled at the mount 36, while reflecting 20% of the output light from the x-ray image intensifier 4 onto the image recorder coupled at the mount 35. A photographic camera or a movie camera may, for example, be coupled at the mount 35, and a video camera may be coupled at the mount 36. Photographic or movie exposures can then be undertaken simultaneously with observation of the output image of the x-ray image intensifier 4 on a television display.

Figure 3:
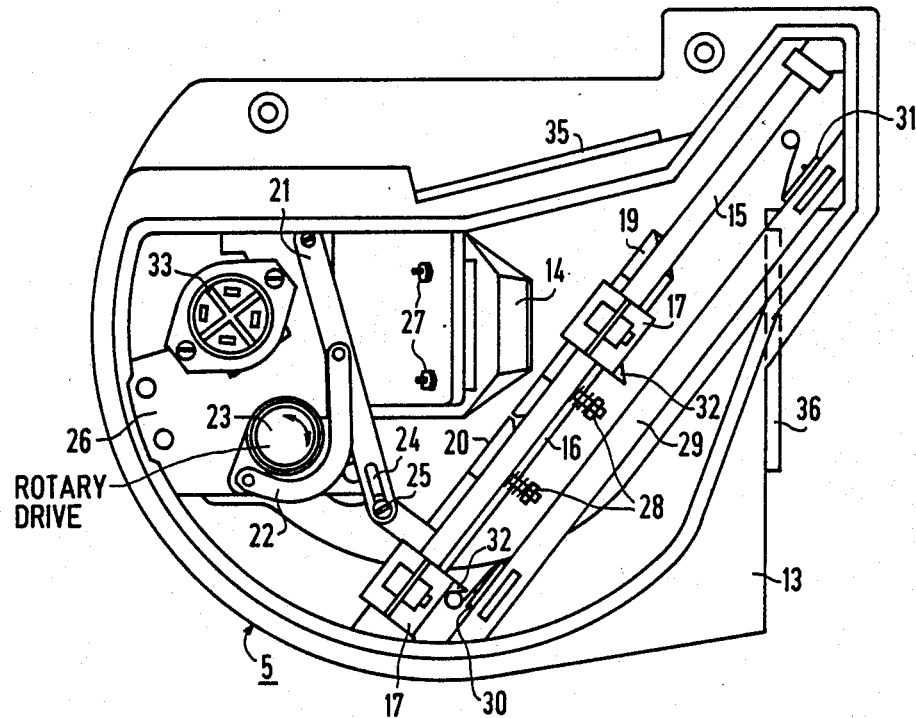
FIG. 3 is a plan view of the two-channel light distributor constructed in accordance with the principles of the present invention shown in FIG. 2.

As best seen in FIG. 3, the crank drive includes a rocker arm 21, a curved arm 22, and a rotary drive 23, such as a motor. The rocker arm 21 is secured to the housing 13 at one end. The other end of the rocker arm 21 has an oblong hole 24 therein, which receives a pin 25 secured to the carriage 16. The rotary drive 23 is connected to the housing 13 by a first carrier 26. The mirrors 8, 10 and 14 can be set in position with respective adjustment screws 27 and 28.

A second carrier 29 is secured to the housing 13 below the carriage 16. The second carrier 29 carriers two microswitches 30 and 31, which function as limit switches for the movable mirrors 8 and 10. The slide 17 of the carriage 16 is provided with a projection 32 which actuates one of the microswitches in the extreme positions of the carriage 16.

A photomultiplier 32 is also secured to the first carrier 26. A small portion of the light from the output of the x-ray image intensifier 4 is coupled laterally to the input of the photomultiplier 33 by a light guide 34 proceeding the first mirror 14. The brightness of the output image of the x-ray image intensifier 4, and thus the x-ray tube emission, can be controlled in a known manner based on the output of the photomultiplier 33.

As can be seen, the arrangement of the components in the light distributor 5 in FIGS. 2 and 3 deflects the beam from the x-ray image intensifier 4 to laterally attached image recorders, so that the combination of the light distributor 5 with the recorders attached thereto has only a small height. Nonetheless, the light distributor 5 has a stable mirror arrangement. Moreover, the light distributor 5 contains only a few simple control components, so that the light distributor 5 has a low weight, and is not particularly susceptible to mechanical disruption.

Figure 4:
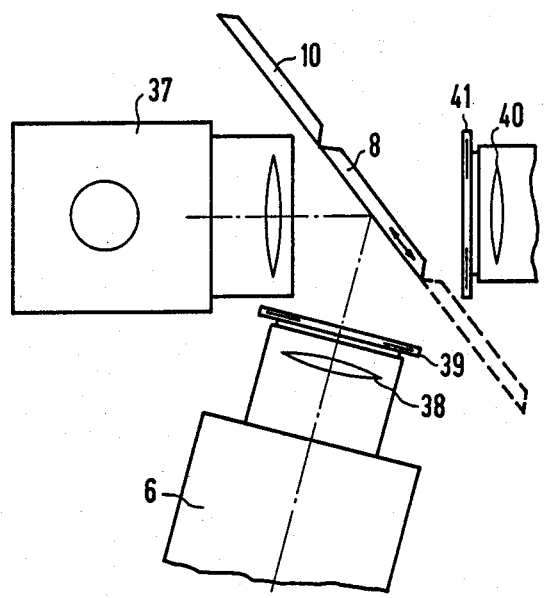
FIG. 4 is a schematic illustration of a further embodiment of a two channel light distributor constructed in accordance with the principles of the present invention.

A further embodiment of a light distributor 5 constructed in accordance with the principles of the present invention is schematically shown in FIG. 4. In this embodiment, instead of the first mirror 14 and instead of using straight-line optics as the input optics, an angular optics 37 is used in FIG. 4, so that the dimension of the light distributor along the direction of the optical axis of the x-ray image intensifier 4 is further reduced, since the length dimensions of the angular optics 37 are less than the combination of the straight line input optics and the mirror 14 in the embodiment of FIGS. 2 and 3. In the embodiment of FIG. 4, a first mirror 8 conducts the beam from the angular optics 37 to optics 38 of a video camera 6, which is preceded by an iris diaphragm 39. If the mirrors 8 and 10 are displaced to the position shown in dashed lines, so that the second mirror 10 is situated in the beam path, a substantial portion of the light is conducted to the optics 40 of a film camera, which may be a photographic camera or a movie camera. This camera may also include a iris diaphragm 41. The smaller portion of the light from the angular optics 37 is, as described above deflected to the video camera 6 for control or monitoring.

Figure 5:
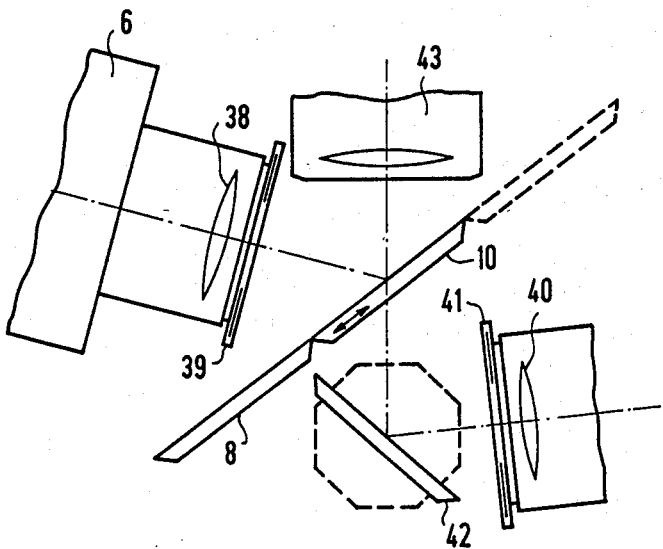
FIG. 5 is a schematic illustration of a multi-channel light distributor constructed in accordance with the principles in the present invention.

A further embodiment of the invention which can adapted for three-channel or four-channel light distribution is schematical shown in FIG. 5. A straight line optics 43 allocated to the x-ray image intensifier 4 is followed by the two moveable mirrors 8 and 10. The light which passes thought the semi-reflecting, second moveable mirror is incident on a third moveable mirror 42, which laterally deflects the light to the optics 40 of a further camera. By rotating the third moveable mirror 42 around an axis parallel to the beam incident thereon, i.e., turning the moveable mirror 42 so as to bring it to the position indicated in FIG. 5 with dashed lines, the light which has passed through the second moveable mirror 10 may, for example, be perpendicularly deflected into or out of the plane of the drawing, so that the light can optionally be conducted to three different image recorders. As a result of using the straight line optics 43 and the three moveable mirror 8, 10 and 42, the image recorders can all be arranged in one plane which is perpendicular to the center axis of the x-ray image intensifier proceeding in the longitudinal direction, so that the dimension of the light distributor in the longitudinal direction can be maintained short in this embodiment as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray diagnostics installation having an x-ray image intensifier with an associated optics system which generates a first beam path for light forming an output image of said x-ray image intensifier, and a plurality of pick-up components for said light, the improvement of a light distributor comprising:

a housing adapted for coupling to said optics system into which said light which comprises said first beam path is admitted;

means in said housing on which said light from said x-ray image intensifier is incident for generating a second beam path of the output image of the x-ray image intensifier;

a carriage;

means for displacing said carriage in a plane disposed obliquely relative to said second beam path so that said carriage does not intersect said second beam path; and first and second mirror surfaces mounted flat on said carriage so that one of said mirror surfaces is moveable into said second beam path upon displacement of said carriage, wherein one of said mirror surfaces is being partially reflecting.

2. An x-ray diagnostics installation as claimed in claim 1, further comprising means for displacing said first and second mirror surfaces into the second beam path.

3. An x-ray diagnostics installation as claimed in claim 1, further comprising an additional mirror surface in said housing and means for pivoting said additional mirror surface into said second beam path.

4. An x-ray diagnostic installation as claimed in claim 3, wherein said additional mirror surface is disposed in said beam path following said first and second mirror surfaces.

5. An x-ray diagnostics installation as claimed in claim 1, wherein said means for displacing said carriage includes two spaced parallel guide rods disposed in the plane of said carriage obliquely to said second beam path and on opposite sides of said means for generating said second beam path, and wherein said carriage has a channeled slide surrounding one of said guide rods and rollers engaging the other of said guide rods.

6. An x-ray diagnostics installation as claimed in claim 1, wherein said means for displacing said carriage includes a crank mechanism in said housing including a rotary drive for operating said crank mechanism, and means for coupling said crank mechanism to said carriage.

7. An x-ray diagnostics installation as claimed in claim 1, wherein said means for generating said second beam path is an angular optical means for laterally deflecting said light from said x-ray image intensifier by an angle with respect to said first beam path.

8. An x-ray diagnostics installation as claimed in claim 7, wherein said angle is approximately 80°.

9. An x-ray diagnostics installation as claimed in claim 1, wherein said means for generating said second beam path is a straight-line optical system, and further comprising a fixed mirror mounted in said housing for laterally deflecting light from said straight-through optical system by an angle with respect to said first beam path.

10. An x-ray diagnostics installation as claimed in claim 9, wherein said angle is approximately 80°.

11. An x-ray diagnostics installation as claimed in claim 1, wherein said partially reflecting mirror is 20% reflective.

12. An x-ray diagnostics installation as claimed in claim 1, further comprising a rotatable mirror surface disposed in said second beam path and following said first and second mirror surfaces, and means for holding said rotatable mirror in one of a plurality of positions, wherein each of said plurality of positions is adapted to deflect said light for forming an output image onto respective image recorder.

13. An x-ray diagnostics installation as claimed in claim 11, wherein one of said mirrors displaceable in said plane obliquely relative to said parallel beam path is a 100% reflective mirror, and the other of said mirrors displaceable in said plane obliquely relative to said parallel beam path is a 20% reflective mirror.

* * * * *